United States Patent [19]

Armenta et al.

[11] Patent Number: 4,668,620

[45] Date of Patent: May 26, 1987

[54] REDUCING BACKGROUND INTERFERENCE ACTIVITY IN ENZYME-LABEL IMMUNOASSAYS

[75] Inventors: Richard Armenta, Mountain View; Ian Gibbons; John Olson, both of Menlo Park, all of Calif.

[73] Assignee: Syntex (U.S.A.) Inc., Palo Alto, Calif.

[21] Appl. No.: 582,355

[22] Filed: Feb. 22, 1984

[51] Int. Cl.$^4$ .......................................... G01N 33/535
[52] U.S. Cl. .......................................... 435/7; 435/14; 435/184; 435/810; 436/801; 436/825
[58] Field of Search ............... 436/825, 801; 435/184, 435/7, 14, 810

[56] References Cited

U.S. PATENT DOCUMENTS

| | | | |
|---|---|---|---|
| 4,434,227 | 2/1984 | Unger | 436/825 X |
| 4,444,880 | 4/1984 | Tom | 436/825 X |
| 4,455,381 | 6/1984 | Magnusson | 436/825 X |
| 4,472,508 | 9/1984 | Ingbar | 436/825 X |
| 4,483,922 | 11/1984 | Carpenter | 435/184 |

FOREIGN PATENT DOCUMENTS 94777  11/1983  European Pat. Off. .

OTHER PUBLICATIONS

Chemical Abstracts, I, 91:153803t (1979).
Chemical Abstracts, II, 94:152970v (1981).

*Primary Examiner*—Sidney Marantz
*Attorney, Agent, or Firm*—Theodore J. Leitereg; Carole F. Barrett

[57] ABSTRACT

Background interference which disrupts the measurement of an analyte in enzyme immunoassays with samples is substantially diminished. In accordance with one embodiment of the invention, the serum sample is treated with a sufficient amount of a peracid compound, either organic or inorganic, for a time and under conditions sufficient to reduce or eliminate background interference contributed by serum components other than analyte. The peracid compound is readily quenched, without adversely affecting the assay compositions. In another embodiment of the invention a liqand for the interfering component of the sample, such as unconjugated enzyme which is inactive but antigenic, is mixed with the sample to be analyzed. The presence of the liqand substantially reduces or eliminates background interference from components of the sample other than analyte.

25 Claims, No Drawings

REDUCING BACKGROUND INTERFERENCE ACTIVITY IN ENZYME-LABEL IMMUNOASSAYS

BACKGROUND OF THE INVENTION

1. Field of the Invention

The use of enzyme labels for the determination of analytes in immunoassays has shown substantial promise and numerous immunoassays have been developed which are dependent upon the accurate measurement of enzymatic activity from an assay medium. One of the problems with this approach concerns factors which contribute to background values.

Background interference can be a serious factor in diminishing the quantitative character of the assay. In many situations, the background interference will vary from sample to sample and will be different in the analyte samples from the standards or calibrators which are employed to provide for translating the observed signal into the concentration of the analyte. In order to enhance the accuracy of the assay, it is desirable to diminish or completely remove the contribution of the background interference to the observed signal during the immunoassay.

2. Description of the Prior Art

Illustrative immunoassays employing enzymes as a label may be found in U.S. Pat. No. 3,817,837 and patents cited therein. Helman, et al., *Clin. Chem.* 20:1193 (1974) published the use of basic hydrogen peroxide for decolorizing hemolyzed and jaundiced serum samples. In U.S. Pat. No. 4,252,783, there is described a method for reducing fluorescent background in fluorescent immunoassays.

SUMMARY OF THE INVENTION

We have found methods for diminishing or eliminating background interference in samples which are assayed for the presence of an analyte by employing an enzyme. We have discovered that the component or components of the sample other than analyte contributing to the background interference appear to specifically interact with the enzyme thereby decreasing the activity of the latter. Such components interfere with the amount of enzymatic activity in the assay medium and thus its relation to the amount of analyte. The background interference can be minimized according to the present invention by incorporating into the sample, prior to performing the assay, an agent for rendering the anti-enzyme components of the sample unreactive toward the enzyme label in an amount and under conditions sufficient to substantially minimize said interference.

In one embodiment of the invention, the sample is treated with a sufficient amount of a peroxide compound for a time and under conditions sufficient to substantially diminish or eliminate the background interference of the sample. Particularly, peracids such as peracetic acid and persulfate, find use under mild conditions, followed by quenching of the peracid without adverse effects on the quantitative nature of the assay. Reduction of background interference in this approach may be enhanced further by incorporating active enzyme into the mixture together with the peracid.

In another embodiment of the invention a ligand for the anti-enzyme component, which ligand may be unconjugated enzyme treated to render it inactive while retaining antigenic character, is incorporated into the sample to be analyzed. Amounts and conditions are chosen to achieve a substantial reduction of the background interference. In the incorporation of such ligand into the serum, reduction in background interference is further enhanced by adding a reducing agent.

DESCRIPTION OF THE SPECIFIC EMBODIMENTS

Methods are provided for diminishing or eliminating background interference in serum samples, which will be subjected to an assay for the determination of analytes wherein measurement of enzyme activity of the sample is employed. The reduction in background interference is greater than about 50%, more usually greater than about 90%, and preferably about 100%.

As mentioned above, we have discovered that a substantial contribution to the background interference in enzyme immunoassays results from a component or components thereof which are capable of specific interaction with the enzyme employed in the assay. For the purposes of this description this component (or components) will be referred to as "anti-enzyme", which means a compound (or compounds) capable of recognizing a particular spatial and polar organization of the enzyme, e.g., antibody to the enzyme. In the method of the invention the serum sample is treated to render the anti-enzyme unreactive toward the enzyme. One method involves contacting at a pH greater than 2 a serum sample with a peracid, either organic or inorganic, in an aqueous medium. For the most part, the peracids are organic percarboxylic acids of from about one to seven carbon atoms, preferably of from one to three carbon atoms, or persulfate. The invention finds particular use in enzyme immunoassays wherein a medium suspected of containing an analyte is brought together with a conjugate of the analyte and an enzyme and with a soluble receptor having sites common to and capable of binding to the analyte and to the particular conjugate. The effect of the medium on the enzymatic activity of the conjugate is analyzed and compared to the effects obtained with samples containing known amounts of analyte.

The amount of peracid employed per milliliter of sample may be varied widely, depending upon the peracid, the period of treatment, as well as the degree of reduction in endogenous anti-enzyme activity desired.

The amount of peracid employed will generally be from about 0.01 mmole to 10 mmole per ml of sample, more usually about 0.1 mmole to 5 mmole per ml of sample. For the organic peracids, the range will generally be from about 0.01 to 10 mmole per ml. For the inorganic acids, the range will generally be from about 0.05 to 10 mmole per ml, more usually from about 0.1 to 5 mmole per ml.

The concentration of the peracid during the incubation with the sample will also vary widely, generally ranging from about 0.01 M to about 1.0 M, more usually from about 0.1 M to about 0.5 M. For the organic peracid, the range will generally be from about 0.05 M to 1.0 M, more usually from about 0.1 M to 0.5 M. For the inorganic acid, the concentration will generally be from about 5 mM to 0.2 M, more usually from about 10 mM to about 0.2 M.

The pH will normally be greater than 2, usually greater than 3, generally from about 2 to 9, more usually from about 3 to 6.

Various buffers may be employed, such as borate, phosphate, glycine, carbonate, Tris, and the like.

When buffer is employed, the concentration of buffer may vary widely, but should be sufficient to maintain the desired pH. Usually, buffer concentrations will generally be from about 0.1 to 1 M, more usually about 0.1 to 0.5 M. The concentration of buffer is not critical and in the case of the organic acid, need not be included during the incubation step.

The treatment method requires combining the sample, the peracid, conveniently as an aqueous solution, and, as desired, buffer. The sample may be subjected to prior treatment, such as filtration, centrifugation, or the like. The peracid may be added as its salt, rather than adding alkali upon combination with the sample as required in addition of the acid itself.

The combined sample and peracid will then be incubated for at least about 1 min, usually not more than about 6 hrs, preferably from about 5 min to 1 hr, more usually from about 5 to 30 min at a temperature of about 4 to 45° C., preferably 20 to 40° C. The particular incubation time, once past the minimum time, is a matter of convenience, and will vary in relation to the amount of peracid used, the amount of components contributing to the background interference, the rate at which these components are rendered inactive by interaction with the peracid, and the stability of the analyte.

The various volumes employed will be determined by the permissible dilution of the sample, e.g., serum, for use in the assay sample. Therefore, the particular concentrations employed, the ratios of volumes of serum, peracid, buffer, and quenching agent, will all be related to the final volume of the assay sample and the desired concentration of the serum in the sample. Usually, about 1 to 20 microliters of peracid (200mM) will be used per 10 microliters of serum.

The materials are combined and agitated in order to insure substantially uniform dispersion, and the mixture incubated at ambient temperatures for the indicated period of time. After the treatment, the assay may then be made directly on the sample by adding whatever appropriate reagents are required for the assay determination.

Illustrative organic peracids include peracetic acid, percarbonic acid ethyl ester, performic acid, and perpropionic acid. For the inorganic acid, potassium persulfate may be used, although any convenient counterion may be employed, particularly any alkali metal cation.

After incubation, the peracid is quenched, conveniently by a reductant, such as sodium sulfite or dithionite. The sodium sulfite will be added as an aqueous solution, generally at a concentration of about 0.1 to 1 M, in an amount sufficient to destroy all of the residual peracid.

In a variant of the above embodiment of the invention, native active enzyme may be mixed with the serum sample to be analyzed and the sample then treated with a peracid under which conditions the enzyme becomes substantially inactivated while still retaining a substantial part of its antigenic nature. The amount of peracid is similar to the amounts used above but is also dependent upon the amount of enzyme added to the sample. Usually about $10^{-11}$ to $10^{-9}$ moles of enzyme will be added to the sample for the conditions described above.

In another embodiment of the invention a ligand for anti-enzyme, such as inactivated enzyme which retains its antigenicity, is employed. The ligand for anti-enzyme may be incorporated into the sample to be analyzed wherein it reacts with anti-enzyme thereby diminishing or eliminating a substantial portion of the background interference in the sample. A ligand specific for the anti-enzyme will be any compound or composition capable of interacting with the anti-enzyme in a manner similar to the way in which the enzyme and anti-enzyme interact thereby reducing or eliminating the interaction between the anti-enzyme and the enzyme. Thus, the ligand for anti-enzyme should be capable of specific interaction with the anti-enzyme by, for example, having a particular spatial and polar organization recognized by the anti-enzyme or being capable of recognizing a particular spatial and polar organization of the anti-enzyme. In either situation the ligand should interact with anti-enzyme and render the latter substantially incapable of interacting with the enzyme. For example, the ligand specific for the anti-enzyme may be the corresponding enzyme, another enzyme capable of interacting with anti-enzyme, antibodies to the anti-enzyme, and the like. The ligand for the anti-enzyme should be non-reactive with other components of the assay medium.

One may prepare inactive but antigenic enzyme in a number of ways. For example, in accordance with the invention the enzyme may first be treated with a peracid compound in an amount and under conditions sufficient to inactivate the enzyme but insufficient to destroy the antigenic character of the enzyme; the so-treated enzyme may then be incorporated into the sample. It is desirable to inactivate substantially all of the activity of the enzyme while retaining a substantial portion of its antigenic character. Generally, a reduction in enzyme activity of greater than about 99% is desired, preferably greater than about 99.99%. In any event, the sufficient amount of inactivated enzyme should be employed, to substantially reduce the anti-enzyme activity when the inactive enzyme is incorporated into the sample to be analyzed.

The method of inactivation of the enzyme is similar to the above-described method for treating a sample with a peracid. Generally, about 90% of antigenic character should be retained, preferably about 99%. The ideal inactive enzyme should be conformationally and antigenically similar to the native enzyme. The amount of residual activity that might be found in the preparation, if any, should be small enough to allow a large molar excess of the inactive enzyme to be present in the assay while contributing only a small amount to the total enzyme activity. The inactive enzyme also must not reactivate.

To inactivate the enzyme directly, the enzyme and peracid are generally incorporated into an aqueous medium in an amount and under conditions sufficient to inactivate substantially all of the enzyme. The amount of peracid employed per ml of solution may be varied widely depending upon the peracid, the period of treatment, the degree of reduction in enzyme activity desired, and the amount of enzyme in the solution.

The amount of peracid employed will generally be from about 0.01 mmoles to 10 mmoles per ml of solution, more usually about 0.1 mmole to 5 mmole per ml of solution, when the solution contains about 1 to 10 mg of enzyme per ml. For the organic peracids the range will generally be from about 0.01 to 10 mmole per ml. For inorganic acids the range will generally be from about 0.05 to 10 mmole per ml, more usually from about 0.1 to 5 mmole per ml. The pH will normally be greater than 2, generally from about 3 to 9, more usually from about 3 to 5, and preferably from about 3 to 3.5.

Various buffers may be employed, such as borate, phosphate, glycine, carbonate, Tris, and the like. When buffer is employed the concentration of buffer may vary widely, but should be sufficient to provide the desired pH. Usually buffer concentrations will generally be from about 0.1 to 1 molar, more usually about 0.1 to 0.5 molar. The concentration of buffer is not critical.

The treatment method requires combining the solution containing the enzyme, the peracid, conveniently as a aqueous solution, and, as desired, buffer. The solution may be subjected to prior treatment such as filtration, centrifugation, or the like. The peracid may be added as a salt, rather than adding alkali upon combination with the solution as required in the addition of peracid itself.

The combined solution and peracid will then be held at a temperature of about 4–37° C., preferably about 20°–25° C., for at least about 1 second, usually not more than about 1 hr, preferably from about 5 seconds to 5 minutes, more usually from about 25 to 35 seconds. The particular time, once past the minimum, is a matter of convenience and will vary in relation to the amount of peracid used, the amount of enzyme in the solution and the rate at which the enzyme activity is reduced.

After incubation the peracid is quenched, conveniently by a reductant such as sodium sulfite or dithionite. The sodium sulfite will be added as an aqueous solution, generally at a concentration of about 0.1 to 1 molar, in an amount sufficient to destroy all of the residual peracid, usually an excess amount. The above described method for inactivating the enzyme but retaining the antigenic character thereof is by way of illustration and not limitation. Methods known to those in the art for inactivating an enzyme while retaining its antigenic character may be used in the present invention. For example, one may heat the enzyme under specific conditions of temperature and time during which the activity of the enzyme is reduced or destroyed but the antigenic character is retained. Other chemical means may be employed to inactivate the enzyme.

The ligand for anti-enzyme is next added to the sample to be analyzed. Generally, the ligand is added in an amount sufficient to substantially reduce the anti-enzyme activity in the sample. Usually the ligand is added in an excess amount so that all of the anti-enzyme activity is removed from the sample. Employing an excess amount of a ligand such as inactive but antigenic enzyme causes few problems in the immunoassay since the ligand added is inactive or non-reactive with the other components of the assay medium. Of course, the amount of such ligand should not be so great as to overwhelm the assay medium with protein material. Normally, the ligand is added in the amount of about 1 to 100 µg per ml of sample to be analyzed, preferably about 10–50 µg per ml of sample. The combined sample and ligand are then incubated for at least about 1 min, usually not more than about 6 hrs, preferably for about 5 min to 1 hr, more preferably from about 10 to 30 min at a temperature of about 4 to 45° C., preferably about 20° to 37° C. The particular amount of ligand and the incubation time will vary in relation to the amount of the ligand added to the sample, the amount of anti-enzyme activity in the sample, and the rate at which the ligand combines with the anti-enzyme activity in the sample.

The decrease in background interference may be enhanced further by the addition of a reducing agent to the assay medium. Particularly preferred are those reducing agents which cyclize on being oxidized and are reactive toward disulfide bonds such as, for example, dithiothreitol and dithioerythritol. Generally, the reducing agent is added in the proportion of about $10^3$ to $10^5$ parts by weight per part by weight of inactive but antigenic enzyme.

The enzyme selected for inactivation will be an enzyme that corresponds to the enzyme which is employed in the assay. In an immunoassay it apparently is the anti-enzyme activity for this particular enzyme in the serum sample to be assayed which results in background interference in the assay. The enzymes of particular importance in the present invention are those acting on glycosyl compounds, for example, glycoside hydrolases: α-amylase, cellulase, lysozyme, β-galactosidase, amyloglucosidase, β-glucuronidase. Particularly preferred is β-galactosidase, which generally requires a macromolecular substrate for maximum sensitivity in a homogeneous enzyme immunoassay. Such macromolecular substrates in the latter case are disclosed in Skold, U.S. Pat. No. 4,268,668, issued May 19, 1981, and Mudhave et al., Enzyme, 25:127–131 (1980), incorporated herein by reference in its entirety. Various other β-galactoside derivatives, well documented and exemplified in the literature, can serve as substrates.

The following is exemplary of immunoassay methods for the determination of an analyte in a serum sample. The sample may first be treated by one of the above approaches to substantially reduce anti-enzyme activity. Next, the sample is combined in an aqueous zone with a conjugate comprising an enzyme and analyte and with a receptor for analyte. On the other hand, reduction in anti-enzyme activity by addition of ligand for anti-enzyme may be carried out at the same time that the sample is combined with the above conjugate. Next, substrate for the enzyme is added. The effect of the combination on the enzymatic activity of the conjugate is analyzed and compared to the effect obtained with samples containing known amounts of analyte to determine the presence and amount of analyte in the sample. It is sometimes desirable to include in the combination a receptor for the receptor for analyte. Generally, such a receptor is employed in an amount sufficient to enhance the detection of the modulation of the enzyme activity during the assays, generally in an excess amount when compared to the amount of receptor for the analyte.

The invention finds use in enzyme immunoassays in general and is particularly applicable for analytes which are high molecular weight proteins especially where the molecular ratio of enzyme to analyte in the conjugate is one or greater, particularly about 1/1 to 10/1. The invention may be employed in assays for high molecular weight proteins having a molecular weight of about 250,000–2,000,000 daltons, preferably about 350,000–1,000,000 daltons, more preferably about 400,000–600,000 daltons, e.g., ferritin.

Generally, as mentioned above, a macromolecular substrate is employed for the enzyme. Usually, in an assay for ferritin the enzyme employed is β-galactosidase, the macromolecular substrate is umbelliferone β-galactose linked to dextran, the receptor for ferritin is anti-ferritin, and the receptor for the receptor for ferritin is anti-anti-ferritin.

In carrying out the subject assays, in order to obtain reproducible results, it is desirable that the critical reagents be provided in predetermined ratios for combination with the assay medium, e.g., in kit form, so as to optimize the sensitivity of the assay. In the assay for an analyte, the critical reagents include enzyme-labeled analyte (conjugate). Besides the desire to have the critical reagents in predetermined proportions, it is frequently desirable that ancillary materials, such as buffer, stabilizers and the like, be included with critical reagents, so that dry powders or concentrates may be diluted to form assay solutions directly, avoiding the necessity of individually weighing the various materials.

In the kit, the reagents will be provided in predetermined ratios so as to substantially optimize the sensitivity of the assay to the concentration range of interest. In addition, included with one or both of the reagents may be buffer, inert proteins, such as albumins, stabilizers, such as sodium azide and the like. Desirably, the reagents are provided as dry powders.

In one embodiment of the present invention, a kit for an enzyme immunoassay for a sample which contains components causing background interference may comprise, for combination with the sample to be assayed, (1) a first composition containing a ligand enzyme conjugate as described above, such as, for example, a conjugate of ferritin and $\beta$-galactosidase, (2) a second composition containing a receptor for the ligand, such as anti-ferritin where the ligand is ferritin, and (3) a third composition containing substrate for the enzyme. A ligand for the components causing background interference (anti-enzyme), such as inactive but antigenic enzyme is present in the first or second composition, for instance, inactive but antigenic $\beta$-galactosidase. The first or second composition further may contain a reducing agent, such as dithioerythritol. The third composition further may include a receptor for the receptor for ligand, such as anti-anti-ferritin.

The following is offered by way of illustration and not by way of limitation.

EXAMPLES

The invention is further demonstrated by the following illustrative examples.

All temperatures are in centigrade. All parts and percents not otherwise indicated are by weight, except for mixtures of liquids, which are by volume. All solutions are aqueous solutions unless otherwise indicated. The following abbreviations are used:

h—hour; NEM—N-ethyl maleimide; MBSE—m-maleimidobenzoyl-N-hydroxysuccinimide ester; DTNB—5,5'-dithiobis-(2-nitro-benzoic acid); EDTA—ethylenediamine tetraacetic acid, disodium salt; DONPG—dextran linked-o-nitrophenylgalactoside (prepared according to the teaching of U.S. Pat. No. 4,268,663; RIA—radioimmunoassay; RSA—rabbit serum albumin; PBS, $N_3Mg$-phosphate buffered saline, azide, magnesium; $PO_4(Na+)$-combination of mono and disodium phosphate; SMCC succinimidyl 4-(N-maleimidomethyl)cyclohexane-1-carboxylate; DUG—dextran liked umbelliferone galactoside (dextran of 40,000 molecular weight with about 14% of its amino groups modified with umbelliferone galactoside groups); EtOH (ethanol); EDCI - ethyl dimethylaminopropyl carbodiimide; and dH20 - distilled water.

Source of materials was as follows

MBSE—Pierce 22310; NEM—Sigma 3876; DMF—Mallincrodt DLRE; DTNB—Sigma D8130; EDTA—Sigma 49C-0507; and SMCC—Pierce 50908.

EXAMPLE I

Preparation of $\beta$Galactosidase/Ferritin Conjugate a. Reaction of succinimidyl 4-(N-maleimidomethyl)-cyclohexane-1-carboxylate (SMCC) with ferritin:

Ferritin (5.0 mg/ml) was dialyzed into 0.05M $PO_4(Na+)$ pH 7.0. SMCC at 100 mg/ml, in dry DMF (used immediately after being made), was added to the ferritin, 2 $\mu$l per mg ferritin. The solution was stirred for 30 minutes at room temperature. The unreacted SMCC was removed by dialyzing the solution against 0.05M $PO_4(Na+)$, 2×21, 3 h per change. An aliquot of the modified ferritin was tested for attached maleimide. The remainder was used for conjugation to $\beta$-galactosidase.

b. Conjugation of $\beta$-galactosidase and ferritin:

One hundred $\mu$l of maleimide-coupled ferritin from above (5 mg/ml) was added, under $N_2$, to 3.5 ml of $\beta$-galactosidase (about 2 mg/ml). This gave a molar ratio of 1:15 (ferritin to $\beta$-galactosidase). $N_2$ was bubbled into the reaction tube for 10 minutes. The tube was sealed tightly and the reaction allowed to proceed 16-18 h at room temperature. Cysteine, 100 $\mu$l of 10 mM in 0.05 M $PO_4(Na+)$ pH 7.0, was added to the tube to react all remaining unconjugated maleimide groups. The reaction mixture was then chromatographed on a Biogel A5m column and activity was screened chromogenically using ONPG.

c. (1) Testing effects of serum on enzyme conjugate activity with DUG (fluorogenic macrosubstrate).

Fluorogenic substrate (DUG) was prepared as follows'

Umbelliferone-3-carboxylic acid ethyl ester was prepared according to the procedure of G. Schuman, H. Hansen, *Archiv der Pharmazie*, 271, 490 (1933). Next, a creased, 3-necked, 24/40 round bottomed flask was fitted with an overhead stirrer in the center neck, a nitrogen inlet with stopcock in the left neck, and a stopper in the right neck. HPLC grade $CH_3CN$ (380 ml) was added to the flask followed by the umbelliferone ester from above (18.31 g, 78.2 mmol). The mixture was heated to dissolve all the solid. Acetobromo-$\alpha$-D-galactose (solid, 39.0 g, 89.7 mmol, Sigma Chemical Co.) was added all at once.

$Ag_2O$ (9.3 g, 80.0 mmol) was then added in spatula portions over a period of 5-10 minutes to the very vigorously stirred solution. When the additions were finished, the mixture was stirred an additional 30 minutes. Stirring was stopped, and the contents were allowed to settle for 2 hours.

The reaction mixture was filtered through a medium frit into a 500-ml suction flask. The filter cake was washed with two 15-ml portions of $CH_3CN$. The combined filtrates were concentrated to a heavy oil. The oil was taken up in 200 ml of $CH_2Clhd 2$ and was washed in a 500-ml separatory funnel with two 50-ml portions of pH 7.0 sodium phosphate buffer (0.1 M phosphate) chilled to 0°, followed by a 25-ml portion of saturated aqueous NaCl. The yellow solution was dried over $MgSO_4$ for 2 hours. The solution was then filtered and concentrated to a heavy oily foam.

To the oily foam was added 50-100 ml of absolute EtOH. The solid which formed was collected on a glass frit and washed with a 10-20-ml portion of EtOH chilled to 0°. The solid was then recrystallized from 225 ml of absolute EtOH to give, after washing with two 10-20-ml portions of EtOH chilled to −15° and drying on the filter and under vacuum, 30.56 g of fine needles. Concentration of the combined EtOH mother liquors (300–350 ml) to 200 ml yielded an additional 1.3 g of pure product.

A total of 31.86 g of tetraacetylgalactosylumbelliferone-3-carboxylic acid, ethyl ester was obtained (72.2%), m.p. 157–158.5°.

The ester tetraacetate from above (28.22 g, 50 mmol, 250 meq of ester) was suspended in 250 ml of absolute EtOH in a 1000-ml round bottom flask under $N_2$. KOH (56 g of 85%, 850 mmol) was weighed into a 250 ml stoppered Erlenmeyer flask. Water (250 ml of deionized $H_2O$) was added to the KOH with swirling and cooling (ice bath). When solution was complete and its temperature had cooled to ~10°, the KOH solution was added to the stirring solution of the ester tetraacetate. Three 12-ml portions of $H_2O$ were used to rinse the KOH Erlenmeyer contents into the reaction flask. The reaction flask was covered by aluminum foil and left to stir overnight.

After 16 h the solution was very slightly turbid. Addition of ~10 ml of $H_2O$ caused clarification.

The solution was acidified with 70.8 ml of ice cold concentrated HCl added very slowly with cooling in an ice bath. The solution was concentrated to ~225–250 ml. A white solid precipitated and was collected in a large fritted glass funnel and washed with two portions of 1 N HCl (15 ml at 0°) and 2 portions of $CH_3CN$ (30 ml). The solid was recrystallized from ~50 ml of near boiling $H_2O$ and the hot solution was filtered. On cooling to room temperature and then to 4° for 2 days a mass of white needles was obtained. These were collected on a glass fritted funnel, washed with $2 \times 10$ ml of ice cold 1 N HCl and $2 \times 20$ ml of $CH_3CN$, and air-dried in the funnel to give 15.5 g (77%) of the galactosylumbelliferyl3-carboxylic acid dihydrate. Concentration and recrystallization of the mother liquor gave an additional 480 mg of product.

Further purification was achieved by recrystallization once or twice from dry, HPLC grade $CH_3CN$. To 1.5 l of refluxing $CH_3CN$ was added 5 g of the acid dihydrate from above that had been dried under vacuum with heating. The mixture was heated near reflux until all the solid dissolved, usually about 4 minutes. The solution was filtered on a pre-heated Buchner funnel into a preheated 2 l. suction flask. The solution was allowed to cool to room temperature sealed from moisture. The flask was placed in the cold room overnight.

The resultant crystals were collected by filtration, washed with three 25-ml portions of $CH_3CN$, and placed under high vacuum to dry. This gave 4.7 g (94%) of galactosyl unbelliferone acid as an anhydrous hydroscopic white solid:

nmr: ($D_2O$) concentration dependent, $\delta 8.7$ (1,s,H4), 7.7 (1,d,H5), 7.17 (1 dd, H6) 7.05 (1,dd,H8), 5.27 (1,m,H1'), 3.8–4.35 (6,m,H2'–6')ppm.

uv: $\lambda max = 333$ nm, $\epsilon = 11,200$ (pH 8.75, phosphate buffer).

Anal. (Dihydrate) Calcd for $C_{16}H_{20}O_{12}$: C ,47.53; H, 4.99.

Found: C, 47.51; H, 4.90.

Anal. (anhydrous) Calcd for $C_{16}H_{16}O_{10}$: C,52.18; H, 4.38

Found: C, 50.39; H, 4.86 (Calcd for 0.75 eq $H_2O$: C, 50.44; H, 4.61).

Aminodextran was prepared by dissolving dextran T40 (101 g) in 1.25 M aqueous sodium chloroacetate (500 ml). A 2.5 M aqueous solution of sodium hydroxide (500 ml) was added. The solution was heated at 80°–85° for 3 hr.

The reaction mixture was allowed to cool. Ethanol (1 l.) was added slowly to the stirred reaction mixture. The dextran began to precipitate after 350 ml had been added. Additional ethanol (2 l.) was added to ensure complete precipitation.

The precipitate separated as a gum. The supernatant was decanted easily. The dextran was purified by three additional precipitations. These were carried out in the following manner. The gum was dissolved in water (750 ml). Ethanol (3 l.) was then added slowly until a permanent cloudiness appeared in the solution, then more rapidly. The gummy precipitate of the dextran was then allowed to settle out overnight.

Carboxymethylated dextran T40 (as a gum, prepared from 100 g dextran T40) was dissolved in water (250 ml). A solution of N,N'-bis-(3-aminopropyl)piperazine (400 g, 2.0 mole) in hydrochloric acid (680 g of 8.52 mmole/g. 5.80 mole) was added. To the resulting solution was added EDCI (201 g, 1.05 mole) in water (250 ml). The reaction was stored at room temperature for 22 hrs. At the end of this period, ethanol (3 l.) was added. The dextran began to precipitate after 1.5 l. had been added. The precipitate was allowed to settle out overnight.

The aminodextran was purified by two additional precipitations. These were carried out as previously described. The final precipitation gave a milky suspension, which coagulated and settled out upon addition of a solution of lithium bromide (25 g) in ethanol (250 ml). The resulting gum was diluted in 1 l and found to be 104 mM in amino groups by assay with trinitrobenzenesulfonic acid. A solution of the aminodextran (1 l of 104 mM, 104 mmole) was treated with $K_2HPO_4$(89g,0.5 mole) to give a solution buffered at pH 8–8.1.

The galactosyl umbelliferone acid from above (281 mg, 0.763 mmole) was weighed quickly into a pear-shaped flask containing a stir bar, and the flask was stoppered to protect the contents from atmospheric moisture. By means of a 10-ml syringe, 6 ml of DMF was added. The flask was stoppered and the mixture stirred to form a homogeneous suspension. EDCI (139.6 mg, 0.72 mmol) and NHS (87.9 mg, 0.764 mmol) were weighed and added to the stirring suspension. A bright yellow-orange solution resulted in the stoppered flask in two to five minutes. The flask was covered with aluminum foil and allowed to stir 2 h. The aminodextran from above (53.78 g of solution) was weighed into a 250 ml, 3-necked, round-bottomed flask containing a football stir bar. The solution was brought to a pH of 8.3 (pH meter) by careful addition of concentrated NaOH. The electrode was rinsed into the flask to recover all the aminodextran.

To the vigorously stirring aminodextran solution was added dropwise from a 20 ml syringe the DMF solution of the galactosylumbelliferone acid NHS ester prepared above. The addition took 5–10 minutes. Three 0.5 ml portions of DMF were used to rinse the residual NHS ester from its reaction flask and the addition syringe into the aminodextran solution The aminodextran flask was then stoppered, covered with aluminum foil, and allowed to stir 3 h.

The solution was then brought to a pH of 5.5 (pH meter) by careful addition of concentrated HCl. After acidification the product was precipitated by slow addition of 170 ml of 95% ethanol to the vigorously stirred solution. Precipitation began after 40 to 60 ml of ethanol had been added. The resultant gum was allowed to settle overnight at 4° in the stoppered flask covered by aluminum foil.

The supernatant was then decanted and discarded. The gum was rinsed with three 20-ml portions of 95% ethanol. The ethanol was drained as thoroughly as possible from the gum. To the crude product was added 10 ml of $H_2O$. The mixture was stirred and after about 1 h a clear, light brown, viscous liquid resulted The liquid was transferred to Spectrapor ® dialysis bags. The bags were dialyzed into 4 liters of an aqueous solution containing 0.01 M $NaH_2SO_4$ and 0.005 M $NaN_3$. Buffer was changed at intervals of 4 to 48 h, and a total of 6 changes were made.

The contents of the bags were then centrifuged for 1 h at 16,000 rpm. The contents were carefully transferred to new tubes and centrifuged a second time. The clear supernatants were filtered through a 0.22 μm Millipore ® filter. The product was analyzed and characterized, $\lambda_{max} = 342.5$ nm (pH = 7.0, 10 mM phosphate buffer), and then stored frozen in aliquots.

To 50 μl of serum was added 50 μl of the conjugate from b above, 20-40 ng/ml (1-2 ng/assay).

The mixture was incubated for 2 h at room temperature. Then, 800 μl of 0.1 mM DUG was added and the agents were mixed.

(2) Testing effects of serum on native enzyme activity with DUG:

The procedure of c (1) above was followed using 50 μl of 1.75×PBS, $N_3$, Mg+0.5% RSA and 50 μl β-galactosidase in place of serum and conjugate, respectively, and 800 ml of 0.02mM DUG in 1.75×PBX, $N_3$, Mg +0.5% RSA.

The fluorescence rate was measured at 37°, 10 second delay, 30 second read.

The results are summarized below.

| Sample | ΔF/30 sec. | |
| --- | --- | --- |
|  | Buffer | Serum |
| β-galactosidase | 250 | 230 |
| β-galactosidase/ferritin | 325 | 260 | d. Inhibition of β-galactosidase/ferritin conjugates by anti-β-galactosidase:

To 50 μl of conjugate (50 ng/ml) prepared as above was added 50 μl of anti-β-galactosidase (sheep anti-β-galactosidase S2256 "Q", 2 mg/ml specific antibody as determined by Ouchterlony) at the following concentrations, 1 ng/ml, 3 ng/ml, 10 ng/ml, 30 ng/ml, 100 ng/ml, 300 ng/ml, 1000 ng/ml.

The mixture was incubated for 10 minutes at room temperature and 800 μl of 0.1 mM DUG (pH 7.0) was added.

The fluorescence rate was measured at 37°, 10 sec. delay, 30 sec. read (all reagents are made in 1.75×PBS, $M_3$, Mg +0.5% PSA). The results are presented as:

$$\text{Residual Activity (\%)} = \left( \frac{\Delta F_{30\,sec} + \text{Anti-}\beta\text{-galactosidase}}{\Delta F_{30\,sec} - \text{Anti-}\beta\text{-galactosidase}} \right) \times 100$$

TABLE

| Anti-β-galactosidase Concentration (ng/ml) | Residual Activity (%) |
| --- | --- |
| 1 | 100 |
| 3 | 98 |

TABLE-continued

| Anti-β-galactosidase Concentration (ng/ml) | Residual Activity (%) |
| --- | --- |
| 10 | 95 |
| 30 | 78 |
| 100 | 55 |
| 300 | 32 |
| 1000 | 15 |

The above data indicate that anti-β-galactosidase has an inhibitory effect on the activity of the β-galactosidase/ferritin.

EXAMPLE II

Pretreatment of Serum Samples with Oxone

Samples of serum (6.7, 2.2, 0.74, 0.25, 0.08, and 0.027 μl) were diluted to 20 μl. Each sample was mixed with 30 μl of 1×PBS, $N_3$, Mg +0.5% RSA and 25 μl of 0.2M Oxone (Oxone is a trademark of Du Pont de Nemours, E. I. & Co. for an acid free-flowing solid containing the active ingredient potassium peroxymonosulfate) in $dH_2O$ (adjusted to pH 3.0 with concentrated NaOH). The mixture was incubated for 10 min. at room temperature and 25 μl of 0.2 M sodium sulfite/$Na_2HPO_4$ in $dH_2O$ was added. The mixture was again incubated for 5 min. at room temperature To the incubated mixture was added 50 μl of the conjugate prepared in accordance with Example I b (20 ng/ml in 1×PBS, $N_3$, Mg +0.5% RSA) and 50 μl of 1×PBS, $N_3$, Mg+0.5% RSA. The mixture was incubated for 2 h at room temperature then 800 μl of 0.1 mM DUG at pH 7.0 in 1.65×PBS, $N_3$, Mg +0.5% RSA was added. Fluorescence was read at 37° C, 10 sec. delay, 30 sec. read, the results were determined as a function of the amount of serum present in the assay expressed as:

$$\begin{array}{l} \% \text{ Activity} \\ \text{remaining} \\ \text{inconjugate} \end{array} = \left( \frac{\Delta F_{30\,sec} + \text{serum dilution}}{\Delta F_{30\,sec} \text{ no serum}} \right) \times 100$$

As a control the above procedure was repeated substituting 25 μl of 1×PBS, $N_3$, Mg +0.5% RSA for the 25 μl of oxone.

The results are summarized as follows:

| | Residual Activity of Conjugate (%) | |
| --- | --- | --- |
| Serum Volume (μl) | Oxone Pretreatment | Control |
| 0.027 | 100 | 95 |
| 0.08 | 100 | 92 |
| 0.25 | 100 | 85 |
| 0.74 | 95 | 70 |
| 2.2 | 82 | 42 |
| 6.7 | 65 | 20 |
| 20 | 40 | 15 |

The above data indicate that pretreatment of the serum sample prior to the assay is an effective means in reducing background interference from components of serum other than analyte.

EXAMPLE III

Ferritin Assay Using Active β-Galactosidase Followed by Oxone to Reduce Background Interference To 10 μl of serum was added 30 μl active native β-galactosidase (330 μg/ml in 1×PBS, $N_3$, Mg and 0.5% RSA) followed by 25 μl of oxone adjusted to pH 3.0 with conc. NaOH, 0.2 M in dH₂O. After stirring, the mixture was incubated for 10 minutes at room temperature. To quench the reaction 25 μl of sodium sulfite/-Na₂HPO₄ (0.2 M) in dH₂O was added and the combination was mixed.

Conjugate with and without anti-ferritin was added to the above to determine the effectiveness of the pretreatment of the serum. Inhibition of conjugate rate was tested by looking at conjugate rate without anti-ferritin present, and the ability of the assay to quantitate ferritin was tested with the anti-ferritin present. The reagents were added as follows:

To 50 μl of conjugate (20–40 ng/ml in 1×PBS, N₃, Mg and 0.5% RSA) was added either 50 μl of goat anti-ferritin (20–40 ng/ml in 1×PBS, N₃, Mg and 0.5% RSA) or 1×PBS, N₃, Mg and 0.5% RSA. The mixture was incubated for 2 hours at room temperature.

Then, 800 μl of 0.2 mM DUG (pH 7.0) containing 10 μg/ml rabbit anti-goat IgG in 1.75×PBS, N₃, Mg and 0.5% RSA was added. Fluorescence rate was read at 37°, 10 sec. delay, 30 sec. read using the Advance ™ Program R30 (Syva Company).

The assay was calibrated with calibrators prepared as follows: Rabbit Anti-human Ferritin (16mg) was attached to 1 g of cyanogen bromide activated Sepharose 4B Beads (Pharmacia batch FE 15337) according to the instructions supplied by the manufacturer.

Pooled human serum (5ml) was added to 0.5 ml of packed beads from above and placed in a large centrifuge tube. The mixture was vortexed and centrifuged immediately (Beckman Centrifuge, 15 minutes, at top speed). The supernatant was decanted and discarded. To the beads was added 50 ml of sera. The tube was rotated for 2 h at room temperature and centrifuged.

Ferritin was added to depeleted serum to give the desired calibrator concentrations The serum calibrators were assayed by RIA to verify ferritin concentration.

The above assay was used to measure ferritin concentration in human serum samples (N). Ferritin concentrations were also measured using a commercial RIA (Clinical Assays). When the results of the two assay methods were compared, a correlation coefficient of 0.94 was found over a range of ferritin concentrations of 6 to 500 mg/ml.

EXAMPLE IV

Ferritin Assay Using Inactivated β-Galactosidase and Dithioerythritol to Reduce Background Interference β-Galactosidase was inactivated as follows: To 10 μl of serum was added 50 μl of the β-galactosidase/ferritin conjugate of Example I b (20–40 ng/ml in 1.75×PBS, N₃, Mg +0.5% RSA) and 30 μl of the inactive β-galactosidase (200 μg/ml and 50 μl of antiferitin (20–40 ng/ml). To this combination was added 10 μl of 50 mM DTE (in 1.75×PBS, N₃, Mg). The mixture was incubated for 2 h at room temperature and 150 μl of 0.7 mM DUG (pH 7.0) containing 10 μg of rabbit anti-goat IgG in 1.75×PBS, N₃, Mg +0.5% RSA and 600 μl 1.75×PBS, N₃, Mg +0.5% RSA.

Fluorescence rate at 37°, 10 sec. delay, 30 sec. read was determined using the Advance ™ (Syva Company, Palo Alto, California).

Ferritin concentrations were measured using both the above method and a commercially available RIA (clinical assays) for human serum samples. Correlations of the results over a range of observed ferritin concentrations from 0 to 200 mg/ml gave a correlation coefficient of 0.97.

What is claimed is:

1. In an assay for determining the presence of an analyte in a sample wherein an enzyme is employed and the amount of analyte is related to the amount of enzyme activity in an assay medium and wherein the sample contains components other than analyte which interfere with the amount of enzyme activity and its relation to the amount of analyte, the improvement which comprises minimizing specific interference resulting from components in the sample other than the analyte which interfere with the amount of enzyme activity and its relation to the amount of analyte by specific binding to the enzyme by incorporating into the sample an agent for rendering said components incapable of binding to the enzyme in an amount and under conditions sufficient to substantially minimize said interference.

2. The method of claim 1 wherein the enzyme is β-galactosidase.

3. The method of claim 1 wherein the agent is a peracid, the sample is serum and the method comprises
(a) contacting the serum, prior to determining the presence of said analyte, with from about 0.01 mmole to 10 mmole of the peracid per ml of serum at a pH of about 2 to 9 for a time sufficient to substantially minimize said interference and
(b) destroying excess peracid with a reductant,
(c) combining the serum with a conjugate of the analyte and an enzyme and with a receptor for analyte, and
(d) determining the enzyme activity of the combination.

4. The method of claim 3 wherein the peracid is organic.

5. The method of claim 3 wherein the peracid is inorganic.

6. The method of claim 3 wherein the peracid is peracetate.

7. The method of claim 3 wherein the inorganic acid is persulfate.

8. The method of claim 3 wherein the analyte is ferritin, the enzyme is β-galactosidase, and the receptor is antibody for ferritin.

9. The method of claim 3 wherein the agent further includes an active enzyme corresponding to the enzyme of the enzyme-analyte conjugate.

10. The method of claim 1 wherein the agent is a ligand capable of interacting with said components in an amount and under conditions sufficient to substantially minimize said interference.

11. The method of claim 10 wherein the ligand is inactive but antigenic enzyme.

12. The method of claim 11 wherein the enzyme is β-galactosidase.

13. The method of claim 10 wherein the sample is further mixed with a reducing agent in an amount and under conditions sufficient to substantially reduce the anti-enzyme activity.

14. The method of claim 13 wherein the reducing agent is dithioerythritol.

15. The method of claim 10 wherein the analyte is ferritin, the enzyme is β-galactosidase, and the receptor is antibody for ferritin.

16. An immunoassay method for the determination of ferritin in serum which comprises:
(a) contacting the serum with from about 0.01 mmole to 10 mmole of a peracid per ml of serum for at least about 1 minute and not more than 6 hrs at a temperature of about 4° to 45° C. and a pH of about 2 to 9, (b) destroying excess peracid with a reductant, (c) combining the serum sample in an aqueous zone with a conjugate comprising β-galactosidase and ferritin and with anti-ferritin and a macromolecular substrate, and (d) determining ferritin in the serum from the modulation of β-galactosidase activity which occurs.

17. The method of claim 16 wherein the serum sample in Step b is further combined with antibody for antibody for ferritin.

18. The method of claim 16 wherein active β-galactosidase is included in Step a.

19. An immunoassay method for the determination of ferritin in serum, which comprises:

(a) combining the serum in an aqueous zone with inactive but antigenic β-galactosidase in an amount of about 1 to 100 micrograms per ml of serum and with a conjugate comprising β-galactosidase and ferritin and with
antibody for ferritin, (b) incubating the combination for a period of about 1 minute to about 6 hours at a temperature of about 4° to 45° C., (c) adding a macromolecular substrate for β-galactosidase to the combination, and (d) determining ferritin in the serum from the modulation of β-galactosidase activity which occurs.

20. The method of claim 19 wherein the serum is further contacted with a reducing agent.

21. The method of claim 20 wherein the reducing agent is dithioerythritol.

22. A kit for an enzyme immunoassay for the determination of ferritin in serum which comprises, in a packaged combination:

a first composition comprising a ferritin/β-galactosidase conjugate, a second composition comprising an antibody for ferritin, and a third composition comprising substrate for β-galactosidase, and inactive but antigenic β-galactosidase in at least one of said first and second compositions.

23. The kit of claim 22 wherein said third composition further comprises an antibody for the antibody for ferritin.

24. The kit of claim 22 wherein said first or second composition further comprises a reducing agent.

25. The kit of claim 22 wherein the reducing agent is dithioerythritol.

* * * * *